United States Patent
Poppe et al.

(10) Patent No.: US 7,592,474 B2
(45) Date of Patent: Sep. 22, 2009

(54) EPOXY FUNCTIONAL SILANES, METHOD FOR THE PRODUCTION THEREOF AND USE OF THE SAME

(75) Inventors: Andreas Poppe, Sendenhorst (DE); Elke Westhoff, Steinfurt (DE); Winfried Stübbe, Greven (DE)

(73) Assignee: BASF Coatings AG, Munster (DE)

( * ) Notice: Subject to any disclaimer, the term of this patent is extended or adjusted under 35 U.S.C. 154(b) by 692 days.

(21) Appl. No.: 10/555,522

(22) PCT Filed: Apr. 23, 2004

(86) PCT No.: PCT/EP2004/004321

§ 371 (c)(1),
(2), (4) Date: Nov. 3, 2005

(87) PCT Pub. No.: WO2004/099220

PCT Pub. Date: Nov. 18, 2004

(65) Prior Publication Data

US 2006/0287545 A1    Dec. 21, 2006

(30) Foreign Application Priority Data

May 8, 2003  (DE) ................................ 103 20 431

(51) Int. Cl.
- *C07F 7/10* (2006.01)
- *C07F 7/04* (2006.01)
- *C07D 303/00* (2006.01)
- *C23C 20/00* (2006.01)

(52) U.S. Cl. ................... 556/411; 556/419; 556/467; 556/482; 549/512; 549/513; 549/556; 106/1.25; 427/133; 427/386; 427/387

(58) Field of Classification Search ............... 549/512, 549/513, 556; 556/411, 419, 467, 482
See application file for complete search history.

(56) References Cited

U.S. PATENT DOCUMENTS 3,927,042 A   12/1975 Gölitz et al. .......... 260/348 SC

| | | | |
|---|---|---|---|
| 6,500,534 B1 | 12/2002 | Dittfurth et al. | 428/323 |
| 6,620,514 B1 | 9/2003 | Arpac et al. | 428/447 |
| 6,632,897 B1 | 10/2003 | Geiter et al. | 526/107 |

FOREIGN PATENT DOCUMENTS

| | | |
|---|---|---|
| DE | 2037617 | 2/1972 |
| DE | 19540623 | 5/1997 |
| DE | 19726829 | 1/1999 |
| DE | 19910876 | 10/2000 |
| EP | 1179575 | 8/2001 |
| WO | WO99/52964 | 10/1999 |
| WO | WO00/35599 | 6/2000 |

OTHER PUBLICATIONS

English language abstract for DE19910876, data from esp@cenet database—Worldwide, 2005.
English language abstract for EP1179575, data from esp@cenet database—Worldwide, 2005.
English language abstract for DE19540623, data from esp@cenet database—Worldwide, 2005.

*Primary Examiner*—Porfirio Nazario Gonzalez
(74) *Attorney, Agent, or Firm*—Cantor Colburn LLP

(57) ABSTRACT

Silanes of the formula:

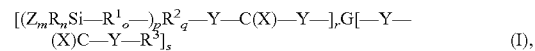

in which m+n=3; m=1, 2 or 3; n=0, 1 or 2; o=0 or 1, and q=1 if o=0; p=1, 2, 3 or 4; q=0 or 1, and p=1 if q=0; r, s=1, 2 or 3; and Z is a hydrolyzable atom or group;
R is a nonhydrolyzable group without an epoxide group;
$R^1$ is a divalent group;
$R^2$ is a (p+1)-valent group;
$R^3$ is a nonhydrolyzable, epoxy-containing group;
X is an oxygen atom and/or sulfur atom;
G is an (r+s)-valent cyclic group;
Y is an oxygen atom, sulfur atom or imino group $>NR^4$ where $R^4$=hydrogen atom, group R, group $(Z_mR_nSi-R^1_o-)_pR^2_q-$, group $R^3-$, group $(Z_mR_nSi-R^1_o-)_pR^2_q-NH-C(X)-$ or group $R^3-NH-C(X)-$;

processes for their preparation, and their use.

20 Claims, No Drawings

US 7,592,474 B2

EPOXY FUNCTIONAL SILANES, METHOD FOR THE PRODUCTION THEREOF AND USE OF THE SAME

CROSS REFERENCE TO RELATED APPLICATIONS

This application is based on PCT/EP2004/004321 filed on 23 Apr. 2004, which claims priority to DE 10320431.8.

FIELD OF THE INVENTION

The present invention relates to new epoxy-functional silanes. The present invention also relates to new processes for preparing epoxy-functional silanes. The present invention further relates to the use of the new epoxy-functional silanes for preparing new condensates, in particular in a new sol-gel process. Furthermore, the present invention relates to the use of the new epoxy-functional silanes as new curable compositions or for preparing them. The present invention relates not least to the use of the new curable compositions for producing new cured compositions, especially coatings and coating systems, and moldings, especially optical moldings, and self-supporting films.

BACKGROUND OF THE INVENTION

Thermally curable compositions based on condensates of epoxy-functional silanes which contain no urethane groups are known from patent applications EP 1 179 575 A2, WO 00/35599 A, WO 99/52964 A, WO 99/54412 A, DE 197 26 829 A1 or DE 195 40 623 A1. They serve in particular for producing highly scratch-resistant coatings. A key feature is that these known thermally curable compositions must have external catalysts or initiators for the reaction of the epoxide groups added to them (cf., e.g., WO 99/52964 A, page 8, line 29, to page 9, line 20) in order that the compositions cure at a practical rate at comparatively low temperatures of 100 to 160° C.

The use of external catalysts, however, is attended by numerous disadvantages. For instance, it severely curtails the processing time or potlife of the known thermally curable compositions.

Where they are to be used to produce coatings with a thickness of more than 20 μm, as typically employed for the clearcoats of automotive OEM coating systems, they must be modified in order that the resulting coatings do not have stress cracks. This is done, as is known, by incorporating flexibilizing structural elements, which accommodate the stresses, into the three-dimensional, organic-inorganic hybrid networks. In order to bring this about, the known, thermally curable compositions, typically present in aqueous alcoholic media, are admixed with binders which are stable in these media. These binders are preferably in the form of aqueous dispersions. These dispersions, however, frequently exhibit a high level of interaction with the catalysts used, and so they cannot be employed together. The result is the removal of many conceivable possibilities for modifying the known thermally curable compositions in an advantageous way.

German patent application DE 199 10 876 A1 discloses thermally curable compositions based on condensates of silanes of the general formula i $$X_m SiR_{1-m} Y_n \qquad (i).$$

In the general formula i the variables X stand for hydrogen, halogen, alkoxy, acyloxy, alkylcarbonyl, alkoxycarbonyl, or —NR'$_2$ (R'=hydrogen and/or alkyl).

The variables R can be identical or different and stand for alkyl, alkenyl, alkynyl, aryl, arylalkyl, alkylaryl, arylalkenyl, alkenylaryl, arylalkynyl or alkynylaryl, it being possible for these radicals to be interrupted by oxygen or sulfur atoms or by the groups —NR'— or —N(H)C(O)O— (urethane) and to carry one or more substituents from the group consisting of halogens and unsubstituted or substituted amino, amide, aldehyde, keto, alkylcarbonyl, carboxyl, mercapto, cyano, hydroxyl, alkoxy, alkoxycarbonyl, sulfonic acid, phosphoric acid, methylacryloyloxy, epoxide and vinyl groups.

The variable Y stands for blocked isocyanate groups.

The indices m and n stand for whole numbers from 1 to 3.

These obligatory silanes can be cocondensed with the optional silanes of the general formula ii $$X_m SiR_{1-m} Z_n \qquad (ii).$$

In this general formula ii the index n stands for a whole number from 1 to 4. The variables X and R are as indicated above. The variables Z stand for hydroxyl, amino, NH(CH$_2$)$_2$NH$_2$ or epoxide groups.

There are, accordingly, a massive number of compounds covered by the general formula i which, moreover, can also be combined with a similarly large number of compounds of the general formula ii.

Furthermore, for the known thermally curable compositions it is essential that they are crosslinked primarily by way of the blocked isocyanate groups. For this, however, particularly high temperatures and long cure times must be employed (cf. DE 199 10 876 A1: Example 1, page 3, line 43: 180° C./45 minutes; Example 2, page 4, line 32: 180° C./30 minutes). Conditions of this kind, however, are completely unsuitable for processes in such economically important fields as that of automotive OEM finishing.

Furthermore, although the known thermally curable compositions produce scratch-resistant cured compositions, the chemical stability of the cured compositions leaves much to be desired.

Additionally, the known epoxy-functional silanes and the condensates prepared from them, and thermally curable compositions, frequently contain ether groups, so that as well as an inadequate chemical resistance the cured compositions produced from the known thermally curable compositions also have an inadequate resistance to actinic radiation, especially UV radiation.

SUMMARY OF THE INVENTION

It is an object of the present invention to provide new epoxy-functional silanes.

The new epoxy-functional silanes ought to be preparable easily and very reproducibly.

The new epoxy-functional silanes ought also to be highly suitable for preparing new condensates, particularly in a sol-gel process.

The new epoxy-functional silanes and their new condensates ought to be more broadly applicable than the known epoxy-functional silanes and their condensates.

In particular the new epoxy-functional silanes and/or their new condensates ought to be outstandingly suitable as curable compositions or for preparing them.

The new curable compositions based on the new epoxy-functional silanes and/or their new condensates ought no longer to have the disadvantages of the prior art but instead ought to cure rapidly at comparatively low temperatures even without external catalysts or initiators. In addition the new curable compositions ought to provide cured compositions, especially coatings and coating systems and also moldings, especially optical moldings, and self-supporting films which not only are highly scratch-resistant, of high gloss, flexible, transparent and clear but also are chemically resistant and resistant to actinic radiation, especially UV radiation.

At the same time the new cured compositions, in particular the coatings and coating systems, in dry film thicknesses >30 µm ought no longer to exhibit stress cracks or delamination from the substrates and ought therefore to be more broadly applicable than the existing curable compositions based on condensates of known epoxy-functional silanes. In particular they should be suitable for producing clearcoats for automotive OEM finishing.

It is an object of the present invention not least to provide new processes for preparing epoxy-functional silanes that can be carried out easily and very reproducibly.

The invention accordingly provides the new epoxy-functional silanes of the general formula I:

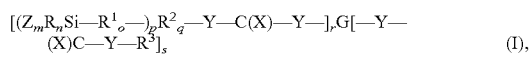  (I), in which the indices stand for zero or whole numbers, $m + n = 3$;

$m = 1, 2$ or $3$;

$n = 0, 1$ or $2$;

$o = 0$ or $1$, and $q = 1$ if $o = 0$;

$p = 1, 2, 3$ or $4$;

$q = 0$ or $1$, and $p = 1$ if $q = 0$;

$r, s = 1, 2$ or $3$;

and the variables are defined as follows:

Z is a hydrolyzable atom, hydroxyl group or hydrolyzable, monovalent, substituted or unsubstituted group;

R is a substituted or unsubstituted, nonhydrolyzable monovalent organic group containing no epoxide group;

$R^1$ is a substituted or unsubstituted, linking, divalent organic group;

$R^2$ is a substituted or unsubstituted, linking, (p+1)-valent organic group;

$R^3$ is a substituted or unsubstituted, nonhydrolyzable, monovalent organic group containing at least one epoxide group;

X is identical or different at each occurrence and is an oxygen atom or sulfur atom;

G is a substituted or unsubstituted, (r+s)-valent organic group;

Y is identical or different at each occurrence and is an oxygen atom, sulfur atom or imino group $>NR^4$ where $R^4$ is identical or different at each occurrence and is a hydrogen atom, group R, group of the general formula II:

  (II), group of the general formula III:

$R^3$—  (III), group of the general formula IV:

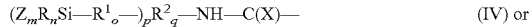  (IV) or group of the general formula V:

$R^3$—NH—C(X)—  (V);

in which the indices and variables are as defined above.

The new epoxy-functional silanes of the general formula I are referred to below as "silanes I of the invention".

The invention also provides the new process for preparing the silanes I of the invention, in which simultaneously or in succession one equivalent of at least one polyiso(thio)cyanate of the general formula VII:

$G(NCX)_{r+s}$  (VII)

in which the variables and indices are as defined above is reacted with r equivalents of at least one compound of the general formula VIII:

  (VIII), in which the variables and indices are as defined above, with the exception of Z=hydrogen atom and hydroxyl group, and with s equivalents of at least one compound of the general formula IX:

$R^3$—YH  (IX)

in which the variables are as defined above, with the exception of Y=imino group $>NR^4$.

The new process for preparing the silanes I of the invention is referred to below as "process 1 of the invention".

The invention further provides the new process for preparing the silanes I of the invention in which simultaneously or in succession one equivalent of at least one compound of the general formula X:

$G(-YH)_{r+s}$  (X)

in which the variables and indices are as defined above, with the exception of Y=imino group $>NR^4$, is reacted with r equivalents of at least one monoiso(thio)cyanate of the general formula XI:

  (XI)

in which the variables and indices are as defined above, with the exception of Z=hydrogen atom and hydroxyl group, and with s equivalents of at least one monoiso(thio)cyanate of the general formula XII:

$R^3$—NCX  (XII), in which the variables are as defined above.

The new process for preparing the silanes I of the invention is referred to below as "process 2 of the invention".

The invention additionally provides the new process for preparing the silanes I of the invention in which simultaneously or in succession one equivalent of at least one compound of the general formula X:

$G$-(—YH)$_{r+s}$  (X)

in which the variables and indices are as defined above and in which at least one group Y=imino group $>NR^4$ is reacted with r equivalents of at least one monoiso(thio)cyanate of the general formula XI:

  (XI)

in which the variables and indices are as defined above, with the exception of Z=hydrogen atom and hydroxyl group; and with s equivalents of at least one monoiso(thio)cyanate of the general formula XIII:

$R^6$—NCX  (XIII)

in which the variable X is as defined above and in which $R^6$=monovalent organic group having at least one carbon-carbon double bond ("double bond"), after which the double bond(s) of the resultant intermediate is or are converted to epoxide groups using an epoxidizing agent.

The new process for preparing the silanes I of the invention is referred to below as "process 3 of the invention".

Collectively the processes 1 to 3 of the invention are referred to as "processes of the invention".

Further subject matter of the invention will emerge from the description.

In the light of the prior art it was surprising and unforeseeable for the skilled worker that the object on which the present invention was based could be achieved by means of the silanes I of the invention and by means of the processes of the invention.

The silanes I of the invention were preparable particularly easily and very reproducibly.

The silanes I of the invention were outstandingly suitable for preparing condensates of the invention, in particular in a new sol-gel process.

The silanes I of the invention and the condensates of the invention were very much more broadly applicable than the known epoxy-functional silanes and their condensates.

In particular the silanes I of the invention and/or the condensates of the invention were outstandingly suitable as new curable compositions or for preparing them.

The curable compositions of the invention based on the condensates and/or silanes I of the invention no longer had the disadvantages of the prior art but instead were curable rapidly at comparatively low temperatures even without external catalysts or initiators. Moreover, the curable compositions of the invention gave new cured compositions, especially new coatings and coating systems and moldings, especially optical moldings, and self-supporting films which not only were highly scratch-resistant, of high gloss, flexible, transparent and clear but also were chemically resistant and resistant to actinic radiation, especially UV radiation.

At the same time the new cured compositions, particularly the coatings and coating systems, in dry film thicknesses >30 µm no longer exhibited any stress cracks or delamination from the substrates and were therefore very much more broadly applicable than the existing curable compositions based on condensates of known epoxy-functional silanes. In particular they were outstandingly suitable for producing clearcoats for automotive OEM finishing.

The processes of the invention were easy, safe and very reproducible in their implementation and gave the silanes I of the invention in particularly high yields.

DETAILED DESCRIPTION OF THE INVENTION

For the purposes of the present invention "autocatalyzed" means that the curing, particularly the thermal curing, of the curable—in particular, thermally curable—compositions of the invention is catalyzed by starting products and/or intermediates which are formed in the course of the cure, in particular the thermal cure (cf. Römpp Online, Georg Thieme Verlag, Stuttgart, 2002, "Autocatalysis").

For the purposes of the present invention external catalysts or initiators are substances which typically catalyze the curing, in particular the thermal curing, of curable, in particular thermally curable, compositions by way of epoxide groups. In the judgement of the art such catalysts are a fundamental prerequisite to achieving proper results (cf. Johan Bieleman, "Lackadditive" [Additives for Coatings], Wiley-VCH, Weinheim, N.Y., 1998, "7.2.4 epoxy resin systems", pages 263 to 269). Further examples of catalysts of this kind which can also be employed in curable, especially thermally curable, compositions based on condensates of epoxy-functional silanes are known from, for example, International Patent Application WO 99/52964 A, page 8 line 29 to page 9 line 20, or from German Patent Application DE 197 26 928 A1, column 3, line 65 to column 4, line 64.

In the context of the present invention "free from external catalysts" means that the compositions of the invention do not contain external catalysts at all or contain them only in amounts which do not color the profile of properties of the compositions of the invention but instead influence it insubstantially, if at all.

In the context of the present invention a sol-gel process is the hydrolysis/condensation process described in Römpp Online, Georg Thieme Verlag, Stuttgart, 2002 "Sol-gel process".

"Hydrolyzable atoms or groups" for the purposes of the invention are atoms or groups which are reactive in the sol-gel process. Accordingly, non-hydrolyzable groups do not participate in the sol-gel process.

In the context of the present invention actinic radiation means electromagnetic radiation, such as near infrared (NIR), visible light, UV radiation, x-rays or gamma radiation, especially UV radiation, or corpuscular radiation, such as electron beams, beta radiation, proton beams, neutron beams or alpha radiation, in particular electron beams.

Combined curing with thermal energy and actinic radiation is referred to in the context of the present invention as "dual cure".

The silanes I of the invention have the general formula I:

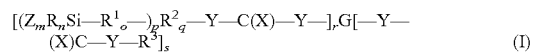

(I)

In the general formula I the indices stand for zero or whole numbers, in particular from 1 to 4, subject to the following conditions:

$$m + n = 3;$$
$$m = 1, 2 \text{ or } 3;$$
$$n = 0, 1 \text{ or } 2;$$
$$o = 0, \text{ or } 1, \text{ and } q = 1 \text{ if } o = 0;$$
$$p = 1, 2, 3 \text{ or } 4;$$
$$q = 0 \text{ or } 1, \text{ and } p = 1 \text{ if } q = 0;$$
$$r, s = 1, 2 \text{ or } 3.$$

Preferably at least one of the following conditions applies:

$$n = 0;$$
$$r = 1;$$
$$q = 0;$$
$$o = 1; \text{ and}$$
$$s = 1;$$

in particular, all these conditions are met simultaneously.

The variable Z denotes a hydrolyzable atom, a hydroxyl group or a hydrolyzable, monovalent, substituted or unsubstituted, in particular organic, group.

Preferably the hydrolyzable atom Z is selected from the group consisting of hydrogen atoms, fluorine atoms, chlorine atoms, bromine atoms and iodine atoms.

Preferably the hydrolyzable, monovalent, substituted or unsubstituted organic group Z has the general formula VI:

$$R^5-W-\qquad\qquad\qquad (VI)$$

In the general formula VI the variable W stands for an oxygen atom, sulfur atom, a carbonyl group or a carboxyl group, in particular for an oxygen atom.

Additionally, in the general formula VI the variable $R^5$ stands for a monovalent organic radical which contains or consists of at least one, in particular one, group selected from the group consisting of substituted and unsubstituted, preferably unsubstituted, branched and unbranched, preferably unbranched, cyclic and noncyclic, preferably noncyclic, alkyl, alkenyl, and alkynyl groups and also substituted and unsubstituted, preferably unsubstituted, aryl groups. In particular use is made of unbranched alkyl groups having 1 to 4 carbon atoms.

Preference is given to using hydroxyl groups and/or groups of the general formula VI, preferably methoxy, ethoxy, propoxy and butoxy groups, especially methoxy and ethoxy groups, as hydrolyzable groups Z.

In the general formula I the variable R stands for a substituted or unsubstituted, especially unsubstituted, nonhydrolyzable, monovalent organic group containing no epoxide group.

The group R preferably contains at least one, especially one, group selected from the group consisting of substituted and unsubstituted, preferably unsubstituted, branched and unbranched, preferably unbranched, cyclic and noncyclic, preferably noncyclic, alkyl, alkenyl, and alkynyl groups, preferably alkyl groups, and also substituted and unsubstituted, preferably unsubstituted, aryl groups, or consists thereof. It is preferred to use unbranched alkyl groups having 1 to 4 carbon atoms, especially methyl and ethyl groups.

In the general formula I the variable $R^1$ stands for a substituted or unsubstituted, preferably unsubstituted, linking, divalent organic group.

The group $R^1$ preferably contains at least one, in particular one, group selected from the group consisting of substituted and unsubstituted, preferably unsubstituted, branched and unbranched, preferably unbranched, cyclic and noncyclic, preferably noncyclic, alkyl, alkenyl, and alkynyl groups and also substituted and unsubstituted, preferably unsubstituted, aryl groups, or consists thereof. In particular the group $R^1$ is an unbranched, noncyclic, unsubstituted, divalent alkyl group having 1 to 10, preferably 2 to 6 and in particular 2 to 4 carbon atoms, such as an ethylene, trimethylene or tetramethylene group.

In the general formula the variable $R^2$ stands for a substituted or unsubstituted, preferably unsubstituted, linking, (p+1)-valent, preferably divalent or trivalent, organic group.

The group $R^2$ preferably contains at least one, especially one, group selected from the group consisting of substituted and unsubstituted, preferably unsubstituted, branched and unbranched, cyclic and noncyclic alkyl, alkenyl, and alkynyl groups, preferably alkyl groups, and also substituted and unsubstituted, preferably unsubstituted, aryl groups, or consists thereof. Examples of suitable groups $R^2$ are ethylene, trimethylene or tetramethylene groups, cyclohexane-1,2-, -1,3-, and -1,4-diyl groups, 1,2-, 1,3-, and 1,4-phenylene groups, propane-1,2,3-triyl groups, cyclohexane-1,2,3-, -1,2-4-, and -1,3,5-triyl groups, and benzene-1,2,2-, -1,2,4-, and -1,3,5-triyl groups.

In the general formula I the variable $R^3$ stands for a substituted or unsubstituted, preferably unsubstituted, nonhydrolyzable, monovalent organic group containing at least one, especially one, epoxide group. The epoxide group is preferably terminal.

The group $R^3$ preferably contains at least one, in particular one, group selected from the group consisting of substituted and unsubstituted, preferably unsubstituted, branched and unbranched, cyclic and noncyclic alkyl, alkenyl, and alkynyl groups, preferably alkyl groups, and also substituted and unsubstituted, preferably unsubstituted, aryl groups, or consists thereof. Examples of suitable groups $R^3$ are 3,4-epoxycyclohex-1-yl, 2-(methylene)oxiran and 2-(phen-1,4-ylene) oxiran groups.

In the general formula I the variable X stands for an oxygen atom and/or sulfur atom. This means that a variable X in a given part of the molecule can be an oxygen atom or a sulfur atom, but independently therefrom in another part of the molecule a variable X can stand for an oxygen atom or a sulfur atom. Put differently, in one silane I of the invention there can be only carbonyl groups or thiocarbonyl groups or both carbonyl groups and thiocarbonyl groups. Preferably all the variables X stand for oxygen atoms.

In the general formula I the variable G stands for a substituted or unsubstituted, (r+s)-valent, preferably divalent or trivalent, especially divalent, organic group.

The group G preferably contains or consists of at least one, especially one, group selected from the group consisting of substituted and unsubstituted, preferably unsubstituted, branched and unbranched, cyclic and noncyclic alkyl, alkenyl, and alkynyl groups, preferably alkyl groups, and also substituted and unsubstituted, preferably unsubstituted, aryl groups.

The group G preferably contains or consists of at least one, especially one, cyclic group.

With particular preference the group G or the cyclic group(s) present in the group G is or are selected from the group consisting of substituted and unsubstituted, heteroatom-containing and heteroatom-free, saturated and unsaturated cycloaliphatic groups and substituted and unsubstituted, heteroatom-containing and heteroatom-free aromatic groups.

Examples of suitable heteroatoms are nitrogen atoms, phosphorus atoms, oxygen atoms, and sulfur atoms, preferably nitrogen atoms and oxygen atoms.

With very particular preference the group G or the cyclic group(s) present in the group G is or are selected from the group consisting of substituted and unsubstituted, heteroatom-free, saturated cycloaliphatic groups and heteroatom-free, substituted and unsubstituted, especially unsubstituted, aromatic groups.

With the greatest preference the heteroatom-free, saturated cycloaliphatic groups are derived from cycloaliphatic compounds selected from the group consisting of substituted and unsubstituted, monocyclic, bicyclic, tricyclic and tetracyclic bridge compounds and spirocyclic compounds.

With the greatest preference the heteroatom-free aromatic groups are derived from aromatic compounds selected from the group consisting of substituted and unsubstituted, monocyclic and polycyclic, condensed and noncondensed aromatics.

In particular the substituted and unsubstituted, monocyclic, bicyclic, tricyclic, and tetracyclic bridge compounds and spirocyclic compounds are selected from the group consisting of cyclopropane, cyclobutane, cyclopentane, cyclohexane, cycloheptane, cyclooctane, p-menthane, m-menthane, o-menthane, 1,1,2,3-tetramethylcyclohexane, 1,1,3,3-tetramethylcyclohexane, thujane, carane, pinane, bornane, nor-carane, norpinane, norbornane, camphane, 2-ethylpinane, 2,4,7,7-tetramethylnorcarane, 2,2-dimethylnorbornane, dicyclohexylmethane, 2,2-dicyclohexylpropane, perhydronaphthalene, perhydroacenaphthene, perhydrophenanthrene, perhydroanthracene, perhydrofluorene, abietane, pimarane, labdane, phyllocladane, gibbane, gonane, cholestane, lanostane, ambrane, onacerane, oleanane, ursane, gammacerane, lupane, bicyclo[3.2.1]octane, bicyclo[5.2.0] nonane, bicyclo[4.3.2]undecane, tricyclo[2.2.1.0$^{2,6}$]heptane, tricyclodecane, tricyclo[5.4.0.0$^{2,9}$]undecane, tricyclo [5.3.2.0$^{4,9}$]dodecane, tricyclo[5.5.1.0$^{3,11}$]tridecane, perhydro-1,4-ethano-5,8-methanoanthracene, adamantane, spiro [3.3]heptane, spiro[3.4]octane, spiro[4.5]decane, spirobicyclohexane and dispiro[5.1.7.2]heptadecane; especially cyclohexane, 1,1,3,3-tetramethylcyclohexane, dicyclohexylmethane, and 2,2-dicyclohexylpropane.

In particular the monocyclic and polycyclic, condensed and noncondensed aromatics are selected from the group consisting of benzene, toluene, xylene, tetramethylxylene, biphenyl, diphenylmethane, 2,2-diphenylpropane, 1,2-, 1,3- or 1,4-diphenylbenzenes(terphenylene), positionally isomeric quaterphenylenes, 1,3,5-triphenylbenzene, naphthalene, acenaphthylene, acenaphthene, phenanthrene, fluorene, anthracene, chrysene, pyrene and fluoranthene; especially benzene, toluene, tetramethylxylene, diphenylmethane, and 2,2-diphenylpropane.

In the general formula I the variables Y are identical or different at each occurrence and stand for oxygen atoms, sulfur atoms and/or imino groups >NR$^4$ with R$^4$ being one of the above-described groups R or a group of the general formula II:

a group of the general formula III:

a group of the general formula IV:

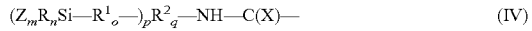

or a group of the general formula V:

in which the indices and variables are as defined above.

The variable Y preferably stands for an oxygen atom, a sulfur atom or an imino group >NR$^4$, more preferably for an imino group >NR$^4$ in which R$^4$ is a group of the general formula II, IV or V, preferably II. In particular R$^4$ is a group of the general formula II if in the general formula the index q=0 and the index o=1.

The groups Z, R, R$^1$, R$^2$, R$^3$, R$^4$, R$^5$ and G and also the below-described group R$^6$ may also be substituted, i.e., may also contain substituents other than alkyl, cycloalkyl, or aryl groups. It is essential in this instance that these other substituents are inert in the sense that they disrupt neither the preparation of the silanes I of the invention, the sol-gel process nor the use of the silanes I of the invention, for example, the crosslinking by way of the epoxide groups, and in particular that they do not inhibit these reactions, trigger them prematurely or lead to unwanted by-products. Examples of suitable other substituents are halogen atoms, especially fluorine atoms, nitrile groups, blocked isocyanate groups which do not undergo deblocking at the temperatures at which the silanes I of the invention are prepared and/or used, alkoxy groups, and alkoxy carbonyl groups.

The groups Z, R, R$^1$, R$^2$, R$^3$, R$^4$, R$^5$ and G and also the below-described group R$^6$ may also contain at least one, preferably one, divalent, linking functional group selected from the group consisting of ether, thioether, carboxylate, thiocarboxylate, carbonate, thiocarbonate, phosphate, thiophosphate, phosphonate, thiophosphonate, phosphite, thiophosphite, sulfonate, amide, amine, thioamide, phosphoramide, thiophosphoramide, phosphonamide, thiophosphonamide, sulfonamide, imide, hydrazide, urethane, thiourethane, urea, thiourea, carbonyl, thiocarbonyl, sulfone, and sulfoxide groups. It is essential here too that the divalent functional groups are inert in the sense that they disrupt neither the preparation of the silanes I of the invention, the sol-gel process nor the use of the silanes I of the invention, for example, the crosslinking by way of the epoxide groups, and in particular that they do not inhibit these reactions, trigger them prematurely or lead to unwanted by-products.

The silanes I of the invention can be prepared by the conventional processes of organic and organosilicon chemistry. The silanes I of the invention are preferably prepared by the processes of the invention.

In the case of process 1 of the invention simultaneously or in succession one equivalent of at least one, especially one, polyiso(thio)cyanate, in particular of a polyisocyanate, of the general formula VII:

in which the variables and indices are as defined above is reacted with r equivalents of at least one, especially one, compound of the general formula VIII:

in which the variables and indices are as defined above, with the exception of Z=hydrogen atom and hydroxyl group, and with s equivalents of at least one, especially one, compound of the general formula IX:

in which the variables are as defined above, with the exception of Y=imino group >NR$^4$.

Examples of suitable polyisocyanates of the general formula VII are the polyisocyanates, preferably the tri- and diisocyanates, especially the diisocyanates, of the above-described acyclic and cyclic, especially cyclic, compounds from which the groups G or the acyclic and cyclic, especially cyclic, groups present in the groups G are derived.

Examples of suitable acyclic diisocyanates to be used in accordance with the invention are trimethylene diisocyanate, tetramethylene diisocyanate, pentamethylene diisocyanate, hexamethylene diisocyanate, ethylethylene diisocyanate or trimethylhexane diisocyanate.

Examples of suitable cyclic diisocyanates for preferred use in accordance with the invention are cyclohexane, dicyclohexylmethane and 2,2-dicyclohexylpropane diisocyanate, 5-isocyanato-1-isocyanataomethyl-1,3,3-trimethylcyclohexane (isophorone diisocyanate, IPDI), diisocyanates derived from dimer fatty acids, as sold under the trade name DDI 1410 by Henkel and described in patents WO 97/49745 A1 and WO 97/49747 A1, especially 2-heptyl-3,4-bis(9-isocyanatononyl)-1-pentylcyclohexane, or 1,2-, 1,4- or 1,3-bis(isocyanatomethyl)cyclohexane, 1,2-, 1,4- or 1,3-bis(2-isocyanatoeth-1-yl)cyclohexane, 1,3-bis(3-isocyanatoprop-1-yl) cyclohexane or 1,2-, 1,4- or 1,3-bis(4-isocyanatobut-1-yl) cyclohexane, benzene, toluene, diphenylmethane, and 2,2-diphenylpropane diisocyanate, and tetramethyl xylidene diisocyanate (TMXDI). Particular preference is given to using IPDI and TMXDI, especially IPDI.

Examples of suitable compounds of the general formula VIII are 2-hydroxyethyltrimethoxysilane, 2-hydroxyethyltriethoxysilane, 3-hydroxypropyl-trimethoxysilane, 3-hydroxypropyltriethoxysilane, bis(2-trimethoxysilylethyl)amine, bis(2-triethoxysilylethyl)amine, bis(3-trimethoxysilylpropyl)amine and bis(3-triethoxysilylpropyl)amine (Dynasilan® 1122 from Degussa), especially bis(3-triethoxysilylpropyl)amine.

Examples of suitable compounds of the general formula IX are glycidol, 1-hydroxy-3,4-epoxycyclohexane and 2-(4-hydroxyphenyl)oxirane, especially glycidol.

In the case of process 2 of the invention one equivalent of at least one, especially one, compound of the general formula X:

$$G(-YH)_{r+s} \quad (X)$$

in which the variables and indices are as defined above, with the exception of Y=imino group >NR$^4$, is reacted with r equivalents of at least one, especially one, monoiso(thio)cyanate, in particular of a monoisocyanate, of the general formula XI:

$$(Z_mR_nSi-R^1{}_o-)_pR^2{}_q-NCX \quad (XI)$$

in which the variables and indices are as defined above, with the exception of Z=hydrogen atom and hydroxyl group, and with s equivalents of at least one, especially one, monoiso(thio)cyanate, in particular of a monoisocyanate, of the general formula XII:

$$R^3-NCX \quad (XII),$$

in which the variables are as defined above.

Examples of suitable compounds of the general formula X are diols, such as 1,2-, 1,3-, and 1,4-dihydroxycyclohexane, pyrocatechol, hydroquinone, bisphenol A and bisphenol F.

Examples of suitable monoisocyanates of the general formula XI are 2-isocyanatopropyltrimethoxy- and -triethoxysilane.

An example of a suitable monoisocyanate of the general formula XII is 2-isocyanatomethyloxirane.

In the case of process 3 of the invention simultaneously or in succession one equivalent of at least one, especially one, compound of the general formula X:

$$G(-YH)_{r+s} \quad (X)$$

in which the variables and indices are as defined above and in which at least one group Y=imino group >NR$^4$, is reacted with r equivalents of at least one, especially one, monoiso(thio)cyanate, in particular of a monoisocyanate, of the general formula XI:

$$(Z_mR_nSi-R^1{}_o-)_pR^2{}_q-NCX \quad (XI)$$

in which the variables and indices are as defined above, with the exception of Z=hydrogen atom and hydroxyl group; and with s equivalents of at least one, especially one, monoiso(thio)cyanate, in particular of a monoisocyanate, of the general formula XIII:

$$R^6-NCX \quad (XIII)$$

in which the variable X is as defined above and in which R$^6$=monovalent organic group having at least one carbon-carbon double bond ("double bond"), after which the double bond(s) of the resultant intermediate is or are converted to epoxide groups using an epoxidizing agent.

Examples of suitable compounds of the general formula X for process 3 of the invention are polyamines, especially diamines, and amino alcohols, such as ethylenediamine, propylenediamine, diethylenetriamine, triethylenetetramine, ethanolamine, and diethanolamine.

Examples of suitable monoisocyanates XIII are vinyl isocyanate, allyl isocyanate, 1-isocyanato-but-3-ene, and 1-(1-isocyanato-1-methylethyl)-3-(1-methylethenyl)-benzene, which is available under the brand name TMI® from the company CYTEC.

Examples of suitable epoxidizing agents are ozone and peroxides, such as m-chloroperbenzoic acid.

One example of a very especially advantageous silane I of the invention is the reaction product of one equivalent of IPDI with one equivalent of bis(3-triethoxysilylpropyl)amine and one equivalent of glycidol.

The silanes I of the invention are outstandingly suitable for preparing condensates of the invention, particularly in a sol-gel process. For that purpose they are subjected to conventional hydrolysis and polycondensation. The condensation is preferably conducted in an aqueous phase. In that case the silane I of the invention can be metered into the aqueous phase or the aqueous phase can be metered into a liquid organic phase comprising or consisting of the silane I of the invention. It is preferred to meter the silane I of the invention into the aqueous phase. With preference the condensation is conducted in the presence of an organic or inorganic acid, particularly an organic acid. The use of acetic acid is preferred. The reaction temperatures at which the condensation is conducted may vary widely; preferably it is conducted at a temperature of from −10 to +50° C., more preferably from 0 to +40° C. and in particular from +10 to +30° C. It is advisable to allow the resulting reaction mixture to afterreact for a period ranging from one hour to three days.

The silanes I of the invention and their condensates of the invention are outstandingly suitable as curable compositions, especially thermally curable or dual-cure compositions, or for preparing them.

The amount of the silanes I of the invention and their condensates of the invention in the compositions of the invention can vary very widely and is guided by their intended use and by the viscosity which is advantageous to the application. The amount is preferably from 10 to 80%, more preferably from 15 to 75%, very preferably from 20 to 70%, and in particular from 25 to 65% by weight, based in each case on the composition of the invention.

The compositions of the invention may comprise at least one modifier. Examples of suitable modifiers are additives such as are typically used in the field, for example, of coating materials, such as binders, crosslinking agents, pigments, substances curable with actinic radiation, reactive diluents, and adjuvants (cf., for example, German Patent Application DE 199 30 665 A1, page 4, line 17 to page 13, line 20). In selecting the modifiers it should be ensured that they do not have any catalytic effect on the crosslinking of the compositions of the invention by way of the epoxide groups, or include any such constituents.

Examples of highly suitable modifiers are binders, particularly in the form of their aqueous dispersions. Especially suitable binders and aqueous dispersions and also the processes for their preparation are known, for example, from German Patent Application DE 199 30 665 A1, page 3, lines 15 to 47 and page 4, line 17 to page 9, line 2.

The amount of the binders in the compositions of the invention may vary very widely and is guided by their intended use and by the hardness and scratch resistance required for that use. The amount is preferably from 0.1 to 20%, more preferably from 0.2 to 15%, very preferably from 0.3 to 12.5%, and in particular from 0.5 to 10% by weight, based in each case on the composition of the invention.

The modifiers can be added before, during or after the condensation of the silanes I of the invention. They are preferably added after the condensation of the silanes I of the invention to the composition of the invention in question. This can be done using conventional mixing techniques and equipment, such as stirred tanks, dissolvers, Ultraturrax, inline dissolvers, stirrer mills or extruders.

The compositions of the invention serve for producing thermally cured or dually cured compositions, especially coatings, coating systems, moldings, especially optical moldings, and self-supporting films.

The coatings, coating systems and self-supporting films here serve in particular to protect surfaces of substrates of any kind against damage due to mechanical and/or chemical exposure, particularly to protect against scratches and against damage by chemicals, and/or for their decoration. The substrates are, in particular, means of transport of any kind, particularly means of transport operated by muscle power, such as cycles or railroad trolleys, aircraft, such as airplanes or airships, marine bodies, such as ships or buoys, rail vehicles, and motor vehicles, such as motor cycles, buses, trucks or automobiles and also parts thereof, constructions, furniture, windows and doors, small industrial parts, coils, freight containers, packaging, white goods, films, optical components, electrical components, mechanical components, and hollow glassware. Further examples of end uses and substrates are known from German Patent Application DE 198 16 136 A1, column 7, line 54 to column 8, line 58.

With particular preference the compositions of the invention are used for producing highly scratch-resistant, chemical-resistant clearcoats as part of automotive OEM finishing with multicoat color and/or effect paint systems. As is known, these particularly high-grade multicoat paint systems are produced by what are termed wet-on-wet processes, as known, for example, from German Patent Application DE 199 30 665 A1, page 15, line 15 to page 16, line 24.

For producing the coatings and coating systems of the invention the compositions of the invention are applied by means of the appropriate techniques conventional for the particular end use, such as by spraying, knife coating, brushing, pouring, dipping, impregnating, trickling or rolling, for example. In the course of such application the substrate to be coated may itself be at rest, with the application equipment or unit being moved. Alternatively, the substrate to be coated, particularly a coil, can be moved, with the application unit being at rest relative to the substrate or being moved appropriately.

For producing the moldings of the invention the compositions of the invention are poured into suitable hollow molds and cured therein, after which they are released from the molds.

For producing the films of the invention the conventional methods such as casting or film blowing are used.

Curing of the compositions of the invention may take place after a certain rest period. This may have a duration of from 30 seconds to 2 hours, preferably from 1 minute to 1 hour, and in particular from 1 to 45 minutes. The rest period serves, for example, for leveling and devolatilization of the coating films or for the evaporation of volatile constituents. The rest period can be assisted and/or shortened by the application of elevated temperatures up to 90° C. and/or by a reduced atmospheric humidity of <10 g water/kg air, in particular <5 g/kg air, provided this does not entail any damage to or change in the compositions of the invention, such as premature complete crosslinking, for instance.

Thermal curing has no particular features as far as its method is concerned but instead takes place in accordance with the conventional methods such as heating in a forced-air oven or irradiation using IR lamps. Thermal curing may also take place in stages. Another preferred method of curing is that of curing with near infrared (NIR) radiation. Particular preference is given to employing a process in which the water constituent is removed rapidly from the wet films. Suitable processes of this kind are described, for example, by Rodger Talbert in Industrial Paint & Powder, 04/01, pages 30 to 33, "Curing in Seconds with NIR", or in Galvanotechnik, Volume 90 (11), pages 3098 to 3100, "Lackiertechnik, NIR-Trocknung im Sekundentakt von Flüssig-und Pulverlacken" [Coating technology, NIR drying within seconds of liquid and powder coatings].

Thermal curing takes place advantageously at a temperature of from 50 to 170° C., more preferably from 60 to 165° C., and in particular from 80 to 150° C. for a time of from 1 minute up to 2 hours, more preferably from 2 minutes up to 1 hour, and in particular from 3 to 30 minutes.

Thermal curing can be supplemented by curing with actinic radiation.

It is surprising that the thermal curing of the compositions of the invention proceeds rapidly and without problems without the use of external catalysts. The absence of external catalysts has the further advantage that the resulting thermally cured compositions of the invention contain no residues of catalyst, which could lead to discoloration, odor problems and/or to damage to substrates and/or to one or more coats of multicoat color and/or effect paint systems.

More surprising still is that, unlike the known cured compositions based on condensates of epoxy-functional silanes, the cured compositions of the invention not only are highly scratch-resistant but also are chemically resistant, particularly resistant toward acids and bases, and resistant to actinic radiation, especially UV radiation.

EXAMPLES

Example 1

The Preparation of an Epoxy-Functional Silane of the General Formula I Containing Urethane Groups In a flask equipped with a reflux condenser and a stirrer 15.34 g of isophorone diisocyanate (0.069 mol) were dissolved under nitrogen in 11.56 g of methyl ethyl ketone and the solution was cooled to 10° C. This was followed by the slow metered addition, with stirring, of 29.38 g (0.069 mol) of bis(3-triethoxysilylpropyl)amine (Dynasilan® 1122 from Degussa). When the addition was at an end the reaction mixture was slowly warmed to room temperature. Then 5.27 g (0.07 mol) of glycidol were metered slowly into the resulting mixture under nitrogen. The resulting reaction mixture was stirred at room temperature for 14 hours and at 60° C. for 10 hours, after which the reaction was at an end (as demonstrated by the disappearance of the isocyanate band from the IR spectrum of the reaction mixture).

Example 2

The Preparation of a Coating Material Based on the Silane I of Example 1 and Production of a Clearcoat from it A reaction vessel equipped with dropping funnel and stirrer was charged with 0.5 part by weight of deionized water, 6.3 parts by weight of 0.1 N acetic acid and 0.75 part by weight of glacial acetic acid. The mixture was slowly admixed, with stirring, with 14.5 parts by weight of the silane I from Example 1. The resulting turbid mixture was stirred at room temperature for 5 hours. After just 4 hours the mixture slowly began to clear and after 5 hours it was completely transparent. The resulting coating material was knife coated onto a glass panel and the resulting film was cured at 140° C. for 22 minutes.

The clearcoat obtained in this way had a dry film thickness of 20 μm. It was free from stress cracks and other surface defects. It was also highly scratch-resistant, a point underlined by means of the steel wool scratch test (rating 1-2).

The steel wool scratch test was carried out using a hammer to DIN 1041 (weight without shaft: 800 g; shaft length: 35 cm). The test panels were stored at room temperature for 24 hours prior to the test.

The flat side of the hammer was wrapped with a ply of steel wool and fastened to the upturned sides using Tesakrepp. The hammer was placed onto the clearcoats at right angles. The weighted part of the hammer was guided over the surface of the clearcoat in a track without tipping and without additional physical force.

For each test, 10 double strokes were performed by hand. After each of these individual tests the steel wool was replaced.

Following exposure, the areas under test were cleaned with a soft cloth to remove residues of the steel wool. The test areas were evaluated visually under artificial light and rated as follows:

| Rating | Damage |
|---|---|
| 1 | None |
| 2 | Slight |
| 3 | Moderate |
| 4 | Moderate to middling |
| 5 | Severe |
| 6 | Very severe |

Evaluation was carried out immediately after the end of the test.

The chemical resistance was tested by means of the BART.

The BART (BASF ACID RESISTANCE TEST) was used to determine the resistance of the clearcoat to acids, alkalis, and water drops. In this test the clearcoat was exposed to a further temperature exposure in a gradient oven after baking at 40° C. for 30 minutes. Beforehand the test substances (sulfuric acid 10% strength, 36% strength; sulfurous acid 6% strength, hydrochloric acid 10% strength, sodium hydroxide solution 5% strength, DI (i.e., fully demineralized or deionized) water—1,2,3 or 4 drops) were applied in a defined manner using a volumetric pipette. After the clearcoat had been exposed to the substances they were removed under running water and the damage was assessed visually after 24 h in accordance with a predetermined scale:

| Rating | Appearance |
|---|---|
| 0 | No defect |
| 1 | Slight marking |
| 2 | Marking/matting/no softening |
| 3 | Marking/matting/color change/softening |
| 4 | Cracks/incipient etching |
| 5 | Clearcoat removed |

Each individual mark (spot) was evaluated and the result was recorded in the form of a rating for each test substance:

| Test Substance | Rating |
|---|---|
| Sulfuric acid 10% strength | 0 |
| Sulfuric acid 36% strength | 0 |
| Hydrochloric acid 10% strength | 1 |
| Sulfurous acid 6% strength | 0 |
| Sodium hydroxide solution 5% strength | 0 |
| Deionized water | 0 |

The clearcoat, accordingly, had a very good chemical resistance.

Example C1 (Comparative)

The Preparation of a Coating Material Based on a Known Epoxy-Functional Silane and Production of a Clearcoat from it 2.78 parts by weight of boehmite (Dispersal® P3 from Sasol Germany GmbH) were added to 25 parts by weight of 0.1 N acetic acid. The resulting mixture was stirred at room temperature until the boehmite had completely dissolved. Then the colloidal solution was treated with ultrasound for 5 minutes.

The resultant homogeneous boehmite sol was admixed with 1 part by weight of glycidyloxypropyltriethoxysilane. The resultant mixture was stirred at room temperature for five hours.

The resultant coating material was knife coated onto a glass panel and the resulting film was cured at 140° C. for 22 minutes.

The resulting clearcoat had a dry film thickness of 20 μm. It was free from stress cracks and other surface defects. It was also extraordinarily scratch-resistant, a point underlined using the steel wool scratch test (rating 1). The chemical resistance, however, left much to be desired. Thus the BART gave the following results:

| Test substance | Rating |
|---|---|
| Sulfuric acid 10% strength | 1 |
| Sulfuric acid 36% strength | 1 |
| Hydrochloric acid 10% strength | 2 |
| Sulfurous acid 6% strength | 1 |
| Sodium hydroxide solution 5% strength | 4 |
| Deionized water | 0 |

What is claimed is:

1. An epoxy-functional silane of the general formula I:

$$[(Z_mR_nSi\text{—}R^1{}_o\text{—})_pR^2{}_q\text{—}Y\text{—}C(X)\text{—}Y\text{—}]_rG[\text{—}Y\text{—}(X)C\text{—}Y\text{—}R^3]_s \quad (I),$$

in which the indices stand for zero or whole numbers, $$m + n = 3;$$

$$m = 1, 2, \text{ or } 3;$$

$$n = 0, 1, \text{ or } 2;$$

$$o = 0, \text{ or } 1, \text{ and } q = 1 \text{ if } o = 0;$$

-continued $p = 1, 2, 3,$ or $4$;

$q = 0$ or $1$, and $p = 1$ if $q = 0$;

$r, s = 1, 2,$ or $3$;

and the variables are defined as follows:
Z is at least one of hydrolyzable atoms, a hydroxyl group hydrolyzable monovalent, substituted groups and hydrolysable monovlaent unsubstituted groups;
R is a substituted or unsubstituted, nonhydrolyzable monovalent organic group containing no epoxide group;
$R^1$ is a substituted or unsubstituted, linking, divalent organic group;
$R^2$ is a substituted or unsubstituted, linking, (p+1)-valent organic group;
$R^3$ is a substituted or unsubstituted, nonhydrolyzable, monovalent organic group containing at least one epoxide group;
X is identical or different at each occurrence and is an oxygen atom or sulfur atom;
G is a substituted or unsubstituted, (r+s)-valent organic group;
Y is identical or different at each occurrence and is an oxygen atom, sulfur atom or imino group $>NR^4$ where $R^4$ is identical or different at each occurrence and is selected from the group consisting of a hydrogen atom, a group of the general formula II:

$$[(Z_mR_nSi-R^1{}_o-)_pR^2{}_q-] \quad (II)$$

a group of the general formula III:

$$R^3- \quad (III),$$

a group of the general formula IV:

$$(Z_mR_nSi-R^1{}_o-)_pR^2{}_q-NH-C(X)- \quad (IV)$$

and a group of the general formula V:

$$R^3-NH-C(X)- \quad (V);$$

in which the indices and variables are as defined above.

2. A silane as claimed in claim 1, wherein the group G comprises at least one cyclic group.

3. A silane as claimed in claim 1, wherein n=0.

4. A silane as claimed in claim 1, wherein r=1.

5. A silane as claimed in claim 1, wherein q=0.

6. A silane as claimed in claim 1, wherein o=1.

7. A silane as claimed in claim 1, wherein s=1.

8. A silane as claimed in claim 1, wherein the group G or the cyclic group(s) present in the group G is or are selected from the group consisting of heteroatom-containing saturated cyclo aliphatic groups, heteroatom-containing unsaturated cyclo aliphatic groups, heteroatom-free, saturated cyclo aliphatic groups, heteroatom-free unsaturated cycloaliphatic groups, heteroatom-containing aromatic groups and heteroatom-free aromatic groups.

9. A silane as claimed in claim 1, wherein the hydrolyzable atom Z is selected from the group consisting of hydrogen, fluorine, chlorine, bromine and iodine atoms and the hydrolyzable monovalent group Z is a hydroxyl group or has the general formula VI:

$$R^5-W- \quad (VI)$$

in which the variables are defined as follows:
W is selected from the group consisting of oxygen atom, sulfur atom, carbonyl group and carboxyl group;

$R^5$ is a monovalent organic radical comprising at least one group selected from the group consisting of substituted and unsubstituted, branched and unbranched, cyclic and noncyclic alkyl, alkenyl, and alkynyl groups, substituted aryl and unsubstituted aryl groups.

10. A silane as claimed in claim 1, wherein the substituted or unsubstituted, nonhydrolyzable, monovalent organic group R containing no epoxide group comprises or consists of at least one group selected from the group consisting of substituted and unsubstituted, branched and unbranched, noncyclic and cyclic alkyl, alkenyl, and alkynyl groups and also substituted and unsubstituted aryl groups.

11. A silane as claimed in claim 1, wherein the substituted or unsubstituted, linking, divalent organic group $R^1$ comprises at least one group selected from the group consisting of substituted and unsubstituted, branched and unbranched, noncyclic and cyclic alkyl, alkenyl, and alkynyl groups, substituted aryl groups and unsubstituted aryl groups.

12. A silane as claimed in claim 1, wherein the substituted or unsubstituted, linking, (p+1)-valent organic group $R^2$ comprises or consists of at least one group selected from the group consisting of substituted and unsubstituted, branched and unbranched, noncyclic and cyclic alkyl, alkenyl, and alkynyl groups, substituted aryl groups and unsubstituted aryl groups.

13. A process for preparing a silane of the general formula I as claimed in claim 1, which comprises simultaneously or in succession reacting one equivalent of at least one polyiso (thio)cyanate of the general formula VII:

$$G(NCX)_{r+s} \quad (VII)$$

in which the variables and indices are as defined above with r equivalents of at least one compound of the general formula VIII:

$$(Z_mR_nSi-R^1{}_o-)_pR^2{}_q-Y-YH \quad (VIII),$$

in which the variables and indices are as defined above, with the exception of Z=hydrogen atom and hydroxyl group, and with s equivalents of at least one compound of the general formula IX:

$$R^3-YH \quad (IX)$$

in which the variables are as defined above, with the exception of Y=imino group $>NR^4$.

14. A process for preparing a silane of the general formula I as claimed in claim 1, comprising simultaneously or in succession reacting one equivalent of at least one compound of the general formula X:

$$G(-YH)_{r+s} \quad (X)$$

in which the variables and indices are as defined above, with the exception of Y=imino group $>NR^4$, with r equivalents of at least one monoiso(thio)cyanate of the general formula XI:

$$(Z_mR_nSi-R^1{}_o-)_pR^2{}_q-NCX \quad (XI)$$

in which the variables and indices are as defined above, with the exception of Z=hydrogen atom and hydroxyl group, and with s equivalents of at least one monoiso (thio)cyanate of the general formula XII:

$$R^3-NCX \quad (XII),$$

in which the variables are as defined above.

15. A process for preparing a silane of the general formula I as claimed in claim 1, which comprises simultaneously or in succession reacting one equivalent of at least one compound of the general formula X:

$$G(-YH)_{r+s} \quad (X)$$

in which the variables and indices are as defined above and in which at least one group Y=imino group >NR$^4$ with r equivalents of at least one monoiso(thio)cyanate of the general formula XI:

$(Z_mR_nSi-R^1_o-)_pR^2_q-NCX$ (XI)

in which the variables and indices are as defined above, with the exception of Z=hydrogen atom and hydroxyl group; and with s equivalents of at least one monoiso(thio)cyanate of the general formula XIII:

$R^6-NCX$ (XIII)

in which the variable X is as defined above and in which R$^6$=monovalent organic group having at least one carbon-carbon double bond ("double bond"), and then converting the double bond(s) of the resultant intermediate to epoxide groups using an epoxidizing agent.

16. A curable composition comprising a silane as claimed in claim 1, an Organic acid, and water.

17. A process for preparing the curable composition as claimed in claim 16 comprising mixing a silane as claimed in claim 18, am organic acid, and water.

18. A thermally cured composition comprising the composition as claimed in claim 16.

19. A coating, coating system, molding, and self-supporting film comprising the thermally cured composition as claimed in claim 18.

20. A process for coating a substrate comprising applying the curable composition of claim 17 onto at least one surface of a substrate, and thermally curing resulting film.

* * * * *